US012564398B2

(12) United States Patent
Lee et al.

(10) Patent No.: US 12,564,398 B2
(45) Date of Patent: Mar. 3, 2026

(54) IMPLANT DEPLOYMENT DEVICE

(71) Applicant: OSTEONIC CO., LTD, Seoul (KR)

(72) Inventors: Dong Won Lee, Seoul (KR); Ui Shik Chung, Bucheon-si (KR); Young Hoon Kwon, Seoul (KR); Dong Uk Moon, Anyang-si (KR)

(73) Assignee: OSTEONIC CO., LTD, Seoul (KR)

( * ) Notice: Subject to any disclaimer, the term of this patent is extended or adjusted under 35 U.S.C. 154(b) by 63 days.

(21) Appl. No.: 18/701,248

(22) PCT Filed: Nov. 1, 2022

(86) PCT No.: PCT/KR2022/016892
§ 371 (c)(1),
(2) Date: Apr. 14, 2024

(87) PCT Pub. No.: WO2023/080592
PCT Pub. Date: May 11, 2023

(65) Prior Publication Data
US 2025/0255600 A1 Aug. 14, 2025

(30) Foreign Application Priority Data
Nov. 2, 2021 (KR) ........................ 10-2021-0148759

(51) Int. Cl.
*A61B 17/04* (2006.01)
(52) U.S. Cl.
CPC .. *A61B 17/0469* (2013.01); *A61B 2017/0464* (2013.01)
(58) Field of Classification Search
None
See application file for complete search history.

(56) References Cited

U.S. PATENT DOCUMENTS 6,066,146 A 5/2000 Carroll et al.
2010/0030236 A1* 2/2010 Hayashi ............. A61B 17/0401
606/232

(Continued)

FOREIGN PATENT DOCUMENTS

JP 2021-522945 A 11/2019
KR 10-2017-0067848 A 6/2017

(Continued)

OTHER PUBLICATIONS

Japanese Office Action dated Feb. 18, 2025 issued on Application No. 2024-522677.

(Continued)

*Primary Examiner* — Shaun L David
(74) *Attorney, Agent, or Firm* — CROWELL & MORING LLP

(57) ABSTRACT

An implant deployment device comprising, a body part comprising a space formed internally in an elongated shape in one direction, a needle having a hollow shape in which a first end engages with a first end of the body part and a second end is formed with a longitudinal slit of a predetermined length, a pushrod movably accommodated in the internal space of the body part in a forward direction, a slider engaging the push rod and comprising a snagging jaw and a receiving groove; and a camrod pivoting between a first position in which the snagging jaw restricts rearward movement of the slider, and a second position in which the snagging jaw is unjammed and inserted into the receiving groove to permit rearward movement of the slider a predetermined distance.

12 Claims, 8 Drawing Sheets

(56)          References Cited

U.S. PATENT DOCUMENTS

| | | |
|---|---|---|
| 2010/0130989  A1 | 5/2010 | Bourque et al. |
| 2020/0078003  A1 | 3/2020 | Bourque et al. |
| 2021/0236113  A1 | 8/2021 | Best et al. |

FOREIGN PATENT DOCUMENTS

| | | |
|---|---|---|
| KR | 10-2017-0077136  A | 7/2017 |
| KR | 2020-0042776  A | 4/2020 |
| KR | 2020-0057132  A | 5/2020 |
| KR | 10-2021-0065132  A | 6/2021 |
| WO | 2021-003281  A | 1/2021 |

OTHER PUBLICATIONS

Decision to grant of the Korean Patent Application No. 10-2022-0143641 (Issued Date: Feb. 26, 2025).
Extended European Search Report issued in European Patent Application No. 22 89 0323 mailed Oct. 6, 2025 (10 pages).

* cited by examiner

IMPLANT DEPLOYMENT DEVICE

CROSS-REFERENCE TO RELATED APPLICATIONS

This application is a National Stage filing under 35 U.S.C. 371 of International Application No. PCT/KR2022/016892, filed on Nov. 1, 2022, which claims the benefit of earlier filing date and right of priority to Korean Application No. 10-2021-0148759, filed on Nov. 2, 2021 in the Korean Intellectual Property Office, the contents of which are all hereby incorporated by reference herein in their entirety.

BACKGROUND OF THE DISCLOSURE

Technical Field

The present invention relates to an implant deployment device, and more particularly to an implant deployment device for deploying an implant for suturing a tear in the knee cartilage (or meniscus) in the event of a tear.

Background Art

Arthroscopic surgery is becoming more common for the repair of soft tissue tears. When the knee cartilage (or meniscus) tears, when the meniscus tears, the lesion is treated by making a microincision at the site of the tear, or by placing an implant with a suture at the site of the tear and securing it with sutures after the lesion is identified with arthroscopy.

Sutures are fixedly attached to the implant to close the lesion. A deployment device in the form of a cannula is used to deploy the implant into the lesion.

The implant deployment device further comprises a cutter for cutting the suture to minimize the length of the suture after closing the lesion with a suture fixedly connected to the implant deployed in the lesion.

In one example, the implants may be configured as a pair. It is important that the implant deployment device is capable of reliably deploying the implant with minimal incision when an operator (a surgeon) uses the implant deployment device to deploy the implant to the lesion site.

SUMMARY OF THE DISCLOSURE

The objective of this invention is to provide an implant deployment device that can deploy an implant stably at the tear site without performing an incisional surgery.

An implant deployment device is provided. The implant deployment device comprising: a body part comprising a space formed internally in an elongated shape in one direction; a needle having a hollow shape in which a first end engages with a first end of the body part and a second end is formed with a longitudinal slit of a predetermined length; a pushrod movably accommodated in the internal space of the body part in a forward direction, which is a direction of the needle, and a rearward direction, which is an opposite direction of the needle, and having a unidirectionally elongate shape, a part of which is accommodated in a hollow portion of the needle and a remaining part of which is accommodated in the internal of the body part; a slider engaging the push rod and comprising a snagging jaw and a receiving groove; and a camrod pivoting between a first position in which the snagging jaw restricts rearward movement of the slider, and a second position in which the snagging jaw is unjammed and inserted into the receiving groove to permit rearward movement of the slider a predetermined distance, wherein a first implant is disposed at the other end of the needle and is pressed by the pushrod as the pushrod moves forward to deploy into an affected area, a second implant disposed rearward of the first implant at the other end of the needle, a lower portion of the second implant is supported by the pushrod and an upper portion of the second implant is accommodated in a slit in the needle.

In one embodiment, the implant deployment device further comprises elastically pressurizing means to elastically pressurize the slider to move rearwardly.

Further, the implant deployment device further comprises a push handle that includes a handle exposed to outside of the body part, penetrates through the body part and engages with the slider to move with the push part, and the push part can be moved by a forward or backward movement of the push handle.

Further, the implant deployment device further comprises a rotary lever, a portion of which is exposed to outside of the body part and a portion of which penetrates through the body part to engage the camrod so as to rotate the camrod, and the camrod can be rotated to a first position or a second position by rotation of the rotary lever.

Further, the implant deployment device can further comprise a length adjustment member engaging the needle at a first end of the body part and movably installed longitudinally of the body part, Further, the needle can be forwardly movable by the length adjustment member.

Preferably, the body part and the length adjustment member are formed with a restraining means that permit forward movement of the length adjustment member and restrict rearward movement of the length adjustment member.

In one embodiment, the restraining means comprises: a first tooth in the shape of a right triangular tooth formed on the body part; and a second tooth in the shape of a right triangularly tooth formed on the length adjustment member and engaging the first tooth, wherein the second tooth can be elastically deformed to allow movement of the length adjustment member when the length adjustment member is moved in a direction of the needle, and wherein movement in the opposite direction can be prevented by the second tooth engaging the first tooth.

In one embodiment, a upper surface of a needle-side end of the push rod is a plane, a lower surface of the second implant is a plane, and the lower surface of the second implant can be supported on the upper surface of the needle-side end of the push rod.

According to the implant deployment device of the present invention, the tear can be reliably closed in a minimally invasive manner without incision.

DETAILED DESCRIPTION OF THE DISCLOSURE

Figure 1:
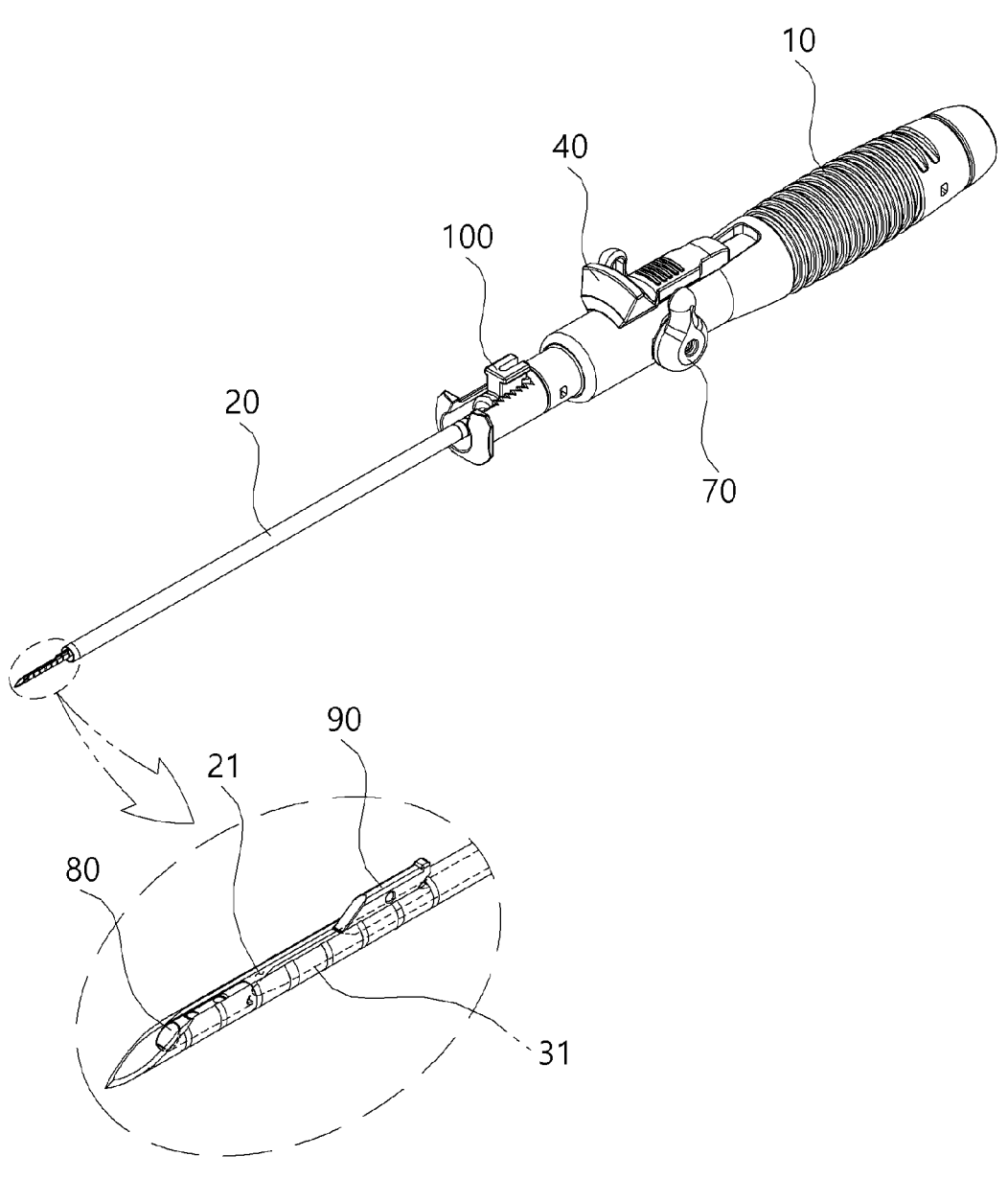
FIG. 1 is a perspective view of the implant deployment device according to an embodiment of this invention.

Hereinafter, specific details for implementing this invention are provided by a detailed description of preferred embodiments, referring to the attached drawings.

Reference numerals are assigned to the components in each drawing, and identical components may have the same numerals, even if they are shown in different drawings.

Figure 2:
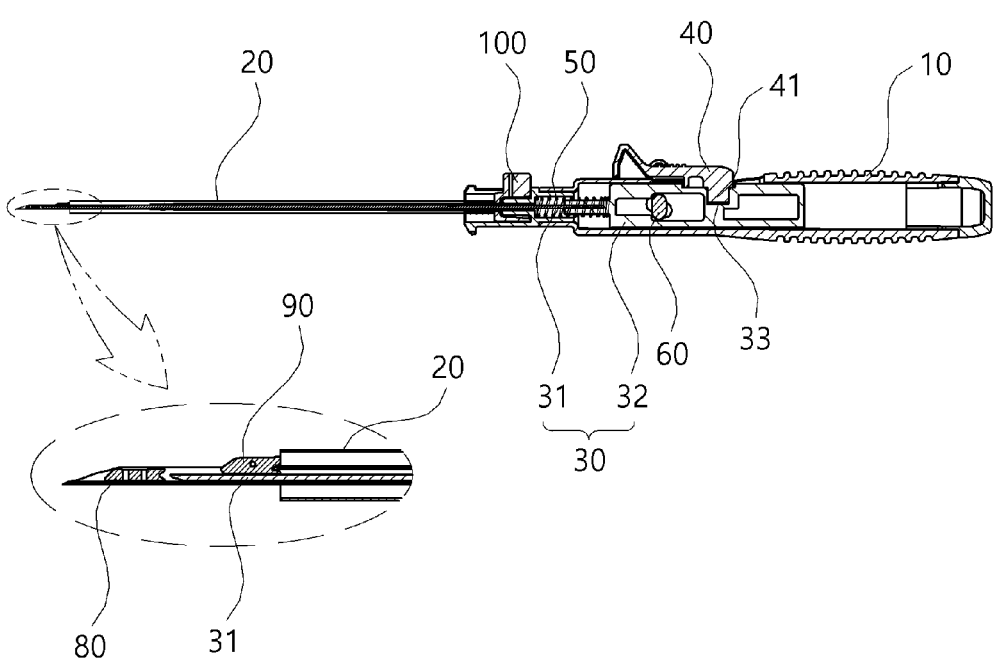
FIG. 2 shows a sectional view of the implant deployment device depicted in FIG. 1.
Figure 3:
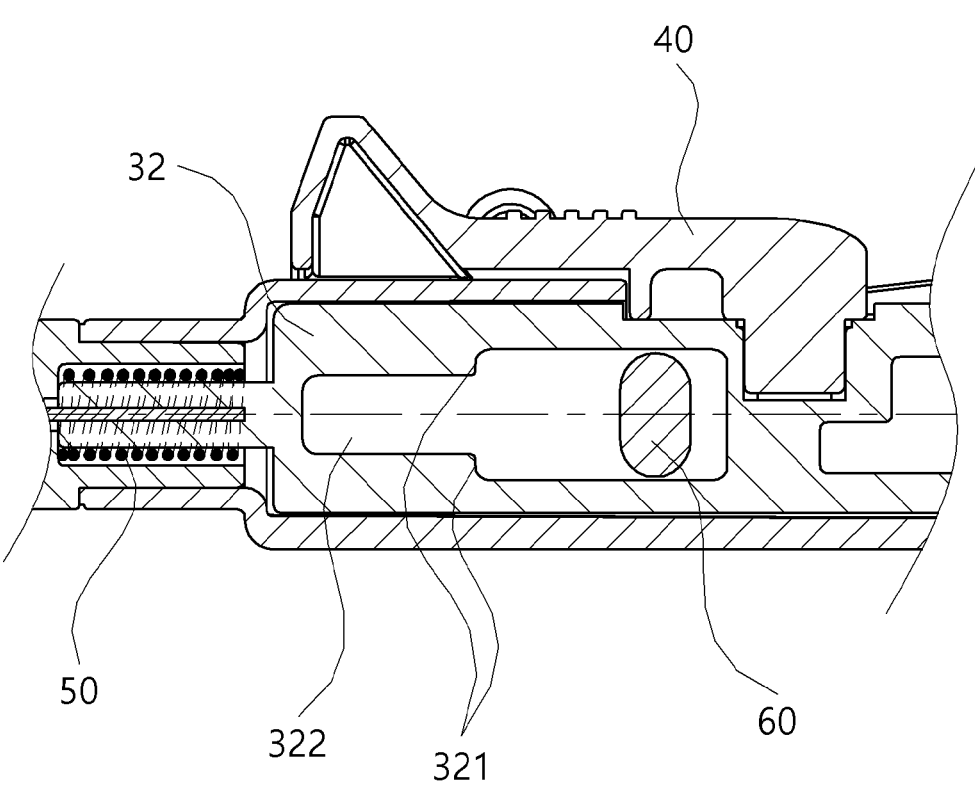
FIG. 3 is a diagram for explaining the forward movement of the push part.
Figure 4:
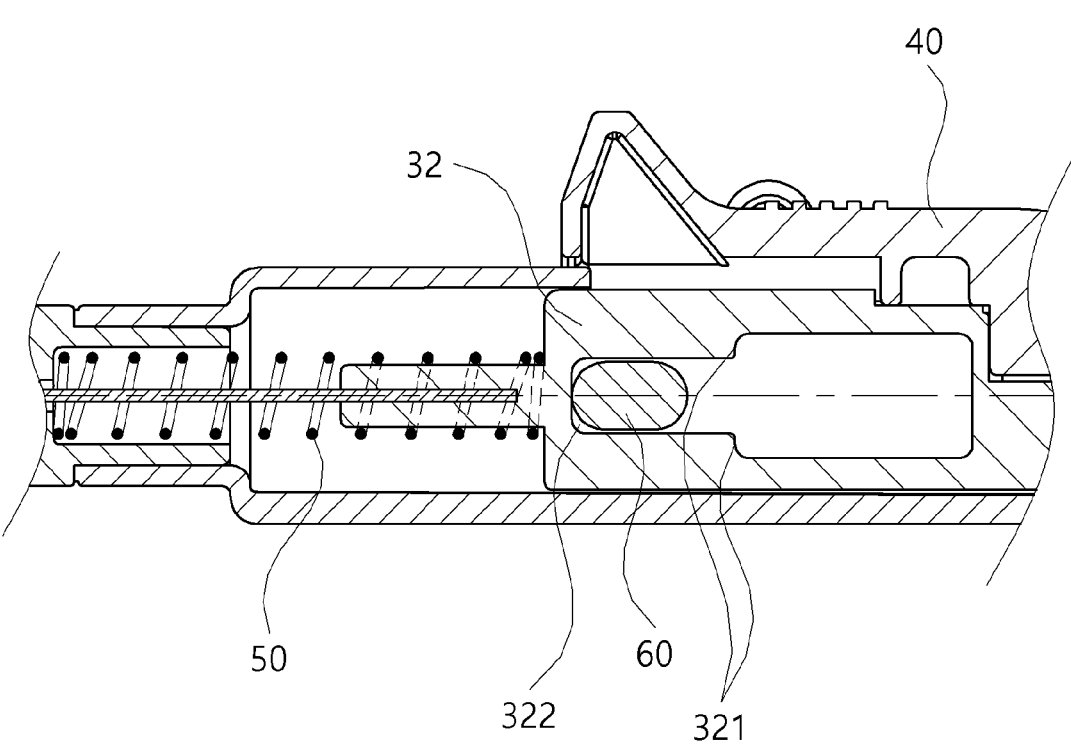
FIG. 4 is a diagram to explain the backward movement of the push part as the camrod rotates to the second position.
Figure 5:
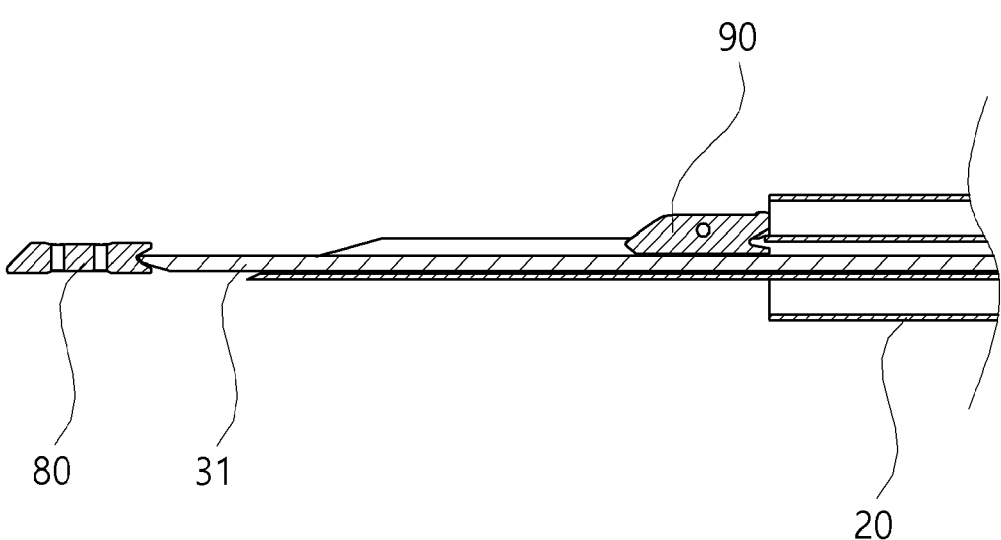
FIG. 5 is a diagram for explaining the deployment of the first implant as the push part moves forward.
Figure 6:
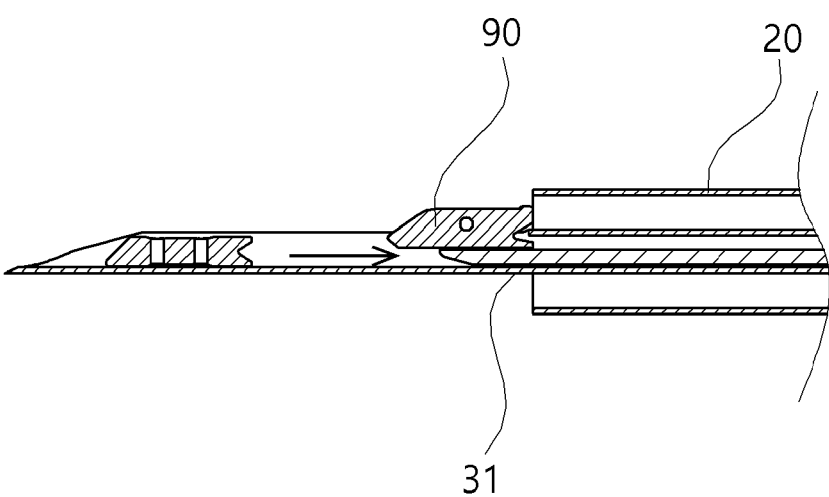
FIG. 6 and FIG. 7 are diagrams for explaining the downward movement of the second implant as the push part moves backward with the camrod rotated to the second position.
Figure 7:
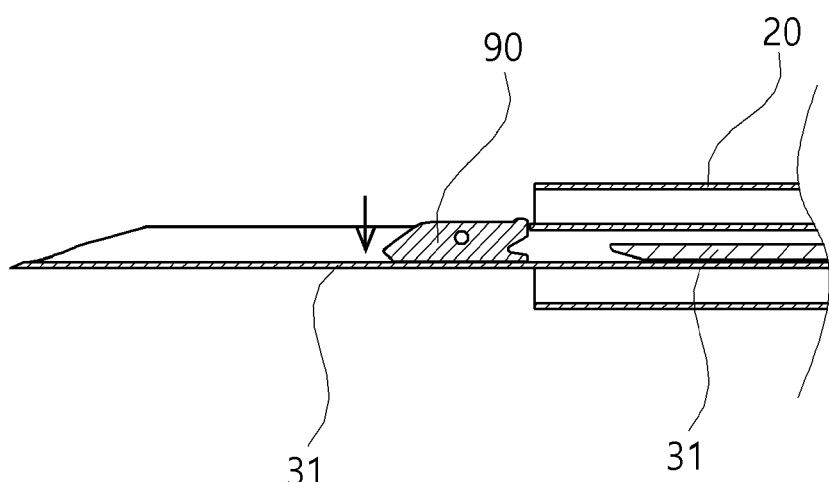
Figure 8:
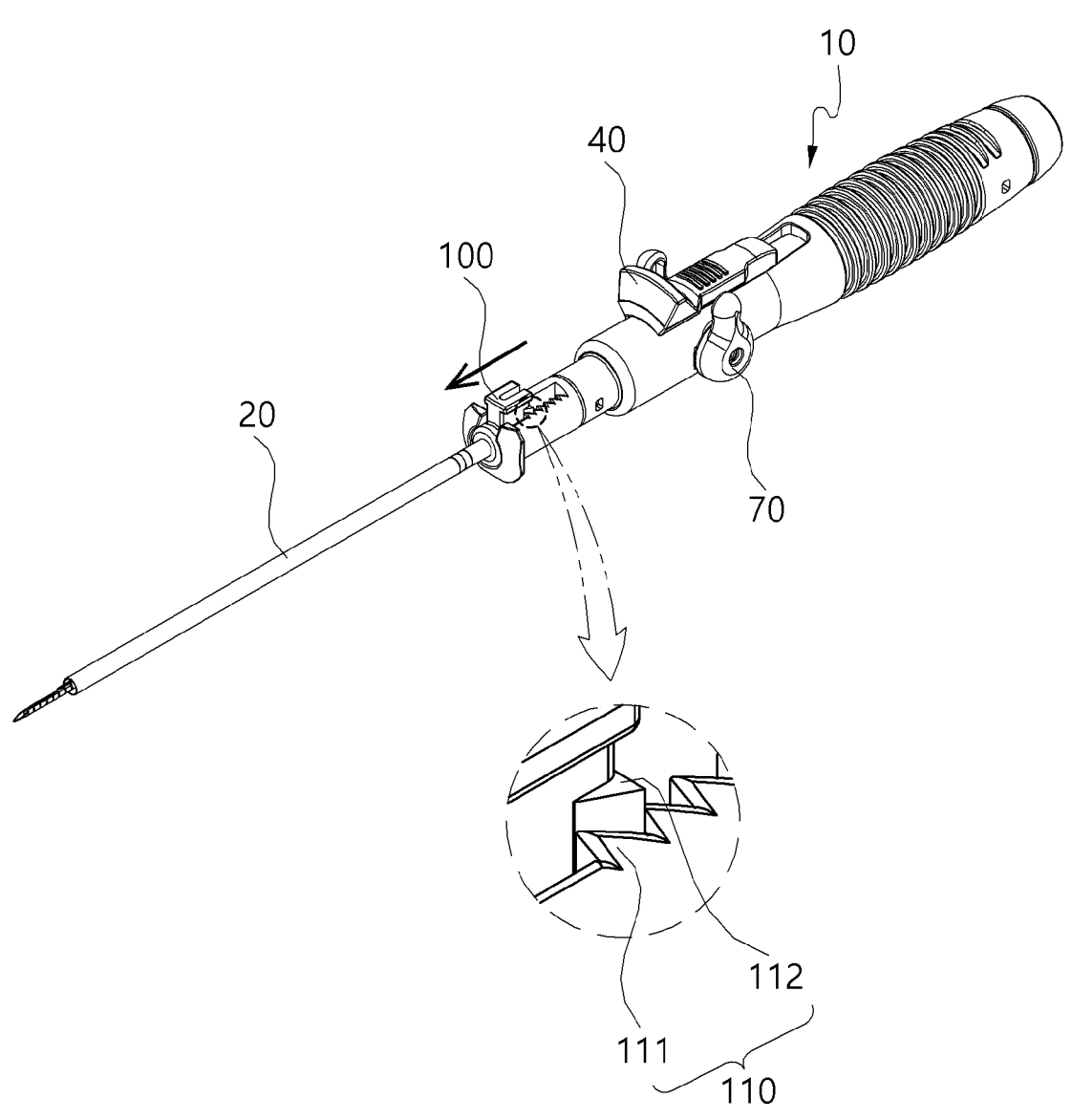
FIG. 8 is a diagram showing the forward movement of the length adjustment member.

FIG. 1 is a perspective view of the implant deployment device according to an embodiment of this invention, FIG. 2 shows a sectional view of the implant deployment device depicted in FIG. 1, FIG. 3 is a diagram for explaining the forward movement of the push part, FIG. 4 is a diagram to explain the backward movement of the push part as the camrod rotates to the second position, FIG. 5 is a diagram for explaining the deployment of the first implant as the push part moves forward, FIGS. 6 and 7 are diagrams for explaining the downward movement of the second implant as the push part moves backward with the camrod rotated to the second position, and FIG. 8 is a diagram showing the forward movement of the length adjustment member.

An implant deployment device according to this embodiment includes a body part 10, a needle 20, a push part 30, a push handle 40, an elastic pressurization means 50, a camrod 60, a rotary lever 70, a first implant 80, and a second implant 90.

The body part 10 includes a space formed inside in a unidirectionally elongated shape as shown in FIG. 1, and the space accommodates a configuration of the slider 31 of the push part 30, the elastomeric pressurization means 50, the camrod 60, and the like.

The body part 10 includes a length adjustment member 100 and a restraining means 110.

The length adjustment member 100 is provided at one end of the body part 10 and is movable to the front of the body part 10. (Movement to the rear is restricted by the restraining means 110 described later.

The length adjustment member 100 is coupled to a needle 20, which is coupled to the body part 10 via the length adjustment member 100.

In FIG. 8, the length adjustment member (100) moved forward, and as the length adjustment member 100 moves forward, the needle 20 moves with it, allowing the needle 20 to penetrate deeper into the skin.

The restraining means 110 can be configured as a ratchet mechanism that allows the length-adjusting member 100 to move forward but restricts its backward movement.

The restraining means 110 includes a first tooth 111 and a second tooth 112.

The first tooth 111 is in the configuration of a right triangular tooth formed on the body part 10, and the second tooth 112 is on the configuration of a right triangular tooth formed in the length adjustment member 100, and is engageable with the first tooth 111.

When the length adjustment member 100 moves forward, the second tooth 112 rides over the first tooth 111 as the length adjustment member 100 or a portion of the body part 10 that abuts the length adjustment member 100 elastically deforms, causing the length adjustment member 100 to move. The rearward movement of the length adjustment member 100 is blocked because the second tooth 112 is caught by the first tooth 111.

The needle 20 is unidirectionally elongated, with one end engaging the first end of the body part 10 and the other end penetrating into the skin to deploy the first implant 80 and the second implant 90, and a longitudinal slit 21 formed at a predetermined length is formed at the other end penetrating into the skin.

The push part 30 includes a push rod 31 and a slider 32.

The pushrod 31 is partially accommodated in the needle 20 and partially accommodated in the interior of the body part 10 in a unidirectionally elongate configuration, movably accommodated forward, which is the direction of the needle 20, and rearward, which is the opposite direction of the needles 20. In FIG. 2, the left side is the front and the right side is the rear.

The upper surface of the other end of the push rod 31 is planar, as shown in FIGS. 3 and 4.

The slider 32 engages the push rod 31 and is accommodated in a space formed in the interior of the body part 10 to move forward or backward, and includes a snagging jaw 321 and a receiving groove 322.

The push handle 40 comprises a handle exposed to the outside of the body part 10, and penetrates through the body part 10 to engage the slider 32, wherein a handle projection 41 of the push handle 40 is inserted into a handle groove 33 of the slider 32, so that the two configurations are joined.

The elastically pressurizing means 50 may utilize a coil spring, as shown, in a configuration that elastically pressurizes the slider 32 to move rearwardly.

The camrod 60 pivots between a first position and a second position, the first position being a position in which the camrod 60 is engaged with the snagging jaw 321 as shown in FIG. 3, restricting the rearward movement of the slider 32, and the second position being a position rotated 90 degrees from the first position as shown in FIG. 4, in which the camrod 60 is disengaged with the snagging jaw 321 and inserted into the receiving groove 322, allowing the slider 32 to move rearwardly a predetermined distance.

The rotary lever 70 is configured to engage the camrod 60 in such a way that when the operator rotates the rotary lever 70, the camrod 60 rotates with it, and like the push handle 40, a portion of the rotary lever 70 is exposed to the outside of the body part 10 and a portion penetrates through the body part 10 to engage the camrod 60.

The first implant 80 is disposed at the other end of the needle 20 and is pressurized by the pushrod 31 as the pushrod 31 moves forward to deploy into the annulus.

The second implant 90 is disposed at the other end of the needle 20 and is positioned posteriorly relative to the first implant 80. The lower surface of the second implant 90 has a planar shape and is supported on the upper surface of the push rod 31, and the upper surface is received in the slit 21 of the needle 20.

Hereinafter, a method of deploying the first implant 80 and the second implant 90 using the aforementioned configurations will be described to illustrate the function, action, and effect of each configuration.

First, in the state shown in FIG. 1, the other end of the needle 20 is inserted into the skin near the torn tissue. Once the needle 20 is inserted, the first implant 80 and the second implant 90 are also inserted. Although not shown, the first implant 80 and the second implant 90 are secured with sutures.

When the push handle 40 is pushed forward with the needle 20 inserted, the elastomeric pressurization means 50 is elastically compressed and the slider 32 coupled to the push handle 40 moves forward, causing the push rod 31 coupled to the slider 32 to move with the slider 32 to press the first implant 80 forward. The first implant 80, pressurized by the push rod 32, moves forward (in the affected area's direction) and is implanted at the operator's desired location. FIG. 5 shows the first implant 80 disengaged from the needle 20.

Once the first implant 80 is implanted, the operator rotates the rotary lever 70 to rotate the camrod 60 to the second position, When the force applied to the push handle 40 is removed, the push rod 31 and the slider 32 are moved rearwardly by the elastomeric pressurization means 50, such that the push rod 31 and the slider 32 are moved further rearwardly as the camrod 60 is inserted into the receiving groove 322 than when the camrod 60 is hung in the receiving groove 322 (see FIG. 2). (See FIG. 4).

As the push rod 31 and slider 32 move rearward as shown in FIG. 4, the second implant 90 moves from the state shown in FIG. 6 to the state shown in FIG. 7, where the second implant 90 is lowered. The second implant 90 is supported by the push rod 31 and when the push rod 31 is moved to the rear, the second implant 90 is moved by gravity to the state shown in FIG. 7.

With the second implant 90 moved downwardly as shown in FIG. 7, pushing the push handle 40 forward causes the push rod 31 and slider 32 to move forward, pushing the second implant 90 forward causes the second implant 90 to move and be implanted in the desired location by the operator, and this is accomplished by the same mechanism as implanting the first implant 80.

On the other hand, if the location where the first implant 80 or the second implant 90 is to be implanted is deeper in the skin, moving the length adjustment member 100 forward as shown in FIG. 8 will cause the needle 20 to move forward as well, allowing the first implant 80 or the second implant 90 to be implanted deeper in the skin than in the condition shown in FIG. 1.

Once the first implant 80 and second implant 90 are implanted, the sutures can be manipulated appropriately to connect the torn tissue.

The foregoing description is merely an exemplary description of the technical ideas of the present invention, and various modifications, changes, and substitutions will be apparent to one of ordinary skill in the art to which the present invention belongs without departing from the essential features of the invention. Accordingly, the embodiments disclosed herein and the accompanying drawings are intended to illustrate and not to limit the technical ideas of the invention, and the scope of the technical ideas of the invention is not limited by these embodiments and accompanying drawings.

What is claimed is:

1. An implant deployment device comprising:
   a body part comprising a space formed internally in an elongated shape in one direction;
   a needle having a hollow shape in which a first end engages with a first end of the body part and a second end is formed with a slit of a predetermined length;
   a push rod being movably accommodated in the internal space of the body part in a forward direction, which is a direction of the needle, and a rearward direction, which is an opposite direction of the needle, a part of which is accommodated in a hollow portion of the needle, a remaining part of which is accommodated in the internal of the body part, and having a unidirectionally elongate shape;

a slider engaging the push rod and comprising:
      a receiving groove formed at a portion of the slider which faces the needle, a rear space positioned rearward of the receiving groove and having a width greater than a width of the receiving groove, and a snagging jaw positioned between the receiving groove and the rear space; and
   a camrod mounted on the body part to pivot about a pivot axis between:
      a first position of the camrod in which the camrod engages the snagging jaw to restrict rearward movement of the slider, and
      a second position of the camrod, the camrod being rotated from the first position by a preset angle, in which engagement between the camrod and the snagging jaw is released and a portion of the camrod is inserted into the receiving groove of the slider, thereby allowing the slider to move rearward by an increased amount as compared to the first position;
   wherein a first implant is disposed at the other end of the needle and is pressed by the push rod as the push rod moves forward to deploy into an affected area, and
   wherein a second implant is disposed rearward of the first implant at the other end of the needle, a lower portion of the second implant being supported by the push rod, and an upper portion of the second implant being accommodated in the slit of the needle.

2. The implant deployment device of claim 1, wherein the implant deployment device further comprises elastically pressurizing means to elastically pressurize the slider to move rearwardly.

3. The implant deployment device of claim 1, wherein the implant deployment device further comprises a push handle that includes a handle exposed to outside of the body part, penetrates through the body part and engages with the slider to move with the push part, and wherein the push part is moved by a forward or backward movement of the push handle.

4. The implant deployment device of claim 3, wherein the implant deployment device further comprises a rotary lever, a portion of which is exposed to outside of the body part and a portion of which penetrates through the body part to engage the camrod so as to rotate the camrod, and wherein the camrod is rotated to a first position or a second position by rotation of the rotary lever.

5. The implant deployment device of claim 3, wherein the implant deployment device further comprises a length adjustment member engaging the needle at a first end of the body part and movably installed longitudinally of the body part, and wherein the needle is forwardly movable by the length adjustment member.

6. The implant deployment device of claim 5, wherein the body part and the length adjustment member are formed with a restraining means that permit forward movement of the length adjustment member and restrict rearward movement of the length adjustment member.

7. The device of claim 6, wherein the restraining means comprises:
   a first tooth in the shape of a right triangular tooth formed on the body part; and
   a second tooth in the shape of a right triangularly tooth formed on the length adjustment member and engaging the first tooth, wherein the second tooth is elastically deformed to allow movement of the length adjustment member when the length adjustment member is moved in a direction of the needle, and wherein movement in the opposite direction is prevented by the second tooth engaging the first tooth.

8. The implant deployment device of claim 1, wherein the implant deployment device further comprises a rotary lever, a portion of which is exposed to outside of the body part and a portion of which penetrates through the body part to engage the camrod so as to rotate the camrod, and wherein the camrod is rotated to a first position or a second position by rotation of the rotary lever.

9. The implant deployment device of claim 1, wherein the implant deployment device further comprises a length adjustment member engaging the needle at a first end of the body part and movably installed longitudinally of the body part, and wherein the needle is forwardly movable by the length adjustment member.

10. The implant deployment device of claim 9, wherein the body part and the length adjustment member are formed with a restraining means that permit forward movement of the length adjustment member and restrict rearward movement of the length adjustment member.

11. The implant deployment device of claim 10, wherein the restraining means comprises:

a first tooth in the shape of a right triangular tooth formed on the body part; and a second tooth in the shape of a right triangularly tooth formed on the length adjustment member and engaging the first tooth, wherein the second tooth is elastically deformed to allow movement of the length adjustment member when the length adjustment member is moved in a direction of the needle, and wherein movement in the opposite direction is prevented by the second tooth engaging the first tooth.

12. The device of claim 1, wherein a upper surface of a needle-side end of the push rod is a plane, a lower surface of the second implant is a plane, and the lower surface of the second implant is supported on the upper surface of the needle-side end of the push rod.

* * * * *